US009265922B2

(12) United States Patent
Barbut et al.

(10) Patent No.: US 9,265,922 B2
(45) Date of Patent: Feb. 23, 2016

(54) SYSTEM AND METHOD FOR IMPROVING OUTCOME OF CEREBRAL ISCHEMIA

(71) Applicants: Denise Barbut, New York, NY (US); Allan Rozenberg, San Diego, CA (US); Axel Heinemann, New York, NY (US)

(72) Inventors: Denise Barbut, New York, NY (US); Allan Rozenberg, San Diego, CA (US); Axel Heinemann, New York, NY (US)

(73) Assignee: ASTUCE, INC., San Diego, CA (US)

( * ) Notice: Subject to any disclaimer, the term of this patent is extended or adjusted under 35 U.S.C. 154(b) by 282 days.

(21) Appl. No.: 13/751,518

(22) Filed: Jan. 28, 2013

(65) Prior Publication Data

US 2013/0269692 A1    Oct. 17, 2013

Related U.S. Application Data

(60) Provisional application No. 61/624,484, filed on Apr. 16, 2012, provisional application No. 61/660,793,
(Continued)

(51) Int. Cl.
*A61M 15/08*    (2006.01)
*A61M 31/00*    (2006.01)
(Continued)

(52) U.S. Cl.
CPC ............ *A61M 31/00* (2013.01); *A61B 17/1204* (2013.01); *A61B 17/12031* (2013.01);
(Continued)

(58) Field of Classification Search
CPC ............ A61M 16/0045; A61M 16/12; A61M 16/0672; A61M 16/202; A61M 16/1015; A61M 16/203; A61M 15/08; A61M 25/003; A61M 25/0032; A61M 25/0068; A61M 16/0409; A61M 16/0486; A61M 16/06; A61M 16/0666; A61M 16/085; A61M 31/00; A61M 13/00; A61M 13/003; A61M 16/0461; A61F 7/12; A61K 31/02; A61K 33/00;
A61K 9/0043; A61B 5/0836; A61B 5/097; A61B 5/6819; A61B 17/1204; A61B 17/12136; A61B 17/12031; A61B 17/12099; A61B 17/12104
USPC ............ 128/203.12, 203.18, 204.22, 204.21, 128/204.18, 204.23, 204.26, 205.24, 128/207.18, 200.26, 203.22, 205.12, 128/205.28, 206.11; 604/19, 26, 101.05, 604/907, 94.01, 173, 284, 95.03, 96.01, 604/101.03, 102.03, 912, 915–916, 919, 96, 604/105; 606/196; 600/532; 607/105
See application file for complete search history.

(56) References Cited

U.S. PATENT DOCUMENTS 3,814,103 A * 6/1974 Fettel et al. ............... 128/207.18
3,867,946 A * 2/1975 Huddy ..................... 128/207.18
(Continued)

FOREIGN PATENT DOCUMENTS

WO    WO 2010/049423 A1    5/2010

OTHER PUBLICATIONS

International Search Report and Written Opinion, issued by the ISA/ United States Receiving Office; regarding corresponding International patent application Serial No. PCT/US2013/037070; dated Aug. 27, 2013, 20 pages.
(Continued)

*Primary Examiner* — Annette Dixon
(74) *Attorney, Agent, or Firm* — Barbara A. Wrigley; Fox Rothschild LLP

(57) ABSTRACT

A system for improving outcome following cerebral ischemia is provided. The system includes a source of nitric oxide and an elongate tubular member for insertion into a nose including at least one orifice thereon. The elongate tubular member is coupled to the source of nitric oxide and configured for delivering the nitric oxide into a nasal cavity through the at least one orifice for absorption into a cerebral vasculature through a nasal vasculature. A device for controlling flow of the gas, a concentration of the nitric oxide in the gas, or both, is also provided.

26 Claims, 11 Drawing Sheets

Related U.S. Application Data filed on Jun. 17, 2012, provisional application No. 61/661,712, filed on Jun. 19, 2012, provisional application No. 61/705,910, filed on Sep. 26, 2012, provisional application No. 61/712,572, filed on Oct. 11, 2012, provisional application No. 61/718,396, filed on Oct. 25, 2012, provisional application No. 61/751,538, filed on Jan. 11, 2013.

(51) Int. Cl.

| | |
|---|---|
| *A61M 25/04* | (2006.01) |
| *A61F 2/958* | (2013.01) |
| *A61M 25/10* | (2013.01) |
| *A61M 16/04* | (2006.01) |
| *A61B 17/12* | (2006.01) |
| *A61K 33/00* | (2006.01) |
| *A61K 9/00* | (2006.01) |
| *A61M 13/00* | (2006.01) |
| *A61M 16/12* | (2006.01) |
| *A61M 16/00* | (2006.01) |
| *A61M 16/06* | (2006.01) |
| *A61B 17/24* | (2006.01) |
| *A61M 16/10* | (2006.01) |

(52) U.S. Cl.
CPC ..... *A61B17/12099* (2013.01); *A61B 17/12104* (2013.01); *A61B 17/12136* (2013.01); *A61K 9/0043* (2013.01); *A61K 33/00* (2013.01); *A61M 13/00* (2013.01); *A61M 13/003* (2013.01); *A61M 16/0461* (2013.01); *A61B 17/12159* (2013.01); *A61B 17/12181* (2013.01); *A61B 17/24* (2013.01); *A61M 16/0672* (2014.02); *A61M 16/12* (2013.01); *A61M 2016/0039* (2013.01); *A61M 2016/1035* (2013.01); *A61M 2202/0275* (2013.01)

(56) References Cited

U.S. PATENT DOCUMENTS

| | | | | |
|---|---|---|---|---|
| 3,903,893 | A * | 9/1975 | Scheer | 606/196 |
| 4,773,410 | A * | 9/1988 | Blackmer et al. | 128/203.26 |
| 4,821,715 | A * | 4/1989 | Downing | 128/207.18 |
| 5,599,304 | A * | 2/1997 | Shaari | 604/94.01 |
| 6,027,478 | A * | 2/2000 | Katz | 604/102.01 |
| 6,142,147 | A * | 11/2000 | Head et al. | 128/204.21 |
| 6,394,093 | B1 * | 5/2002 | Lethi | 128/207.18 |
| 6,848,448 | B1 | 2/2005 | St. Germain et al. | |
| 6,942,686 | B1 | 9/2005 | Barbut et al. | |
| 7,340,298 | B1 | 3/2008 | Barbut | |
| 7,563,772 | B2 | 7/2009 | Mochly-Rosen et al. | |
| 7,729,759 | B2 | 6/2010 | Shalev et al. | |
| 7,861,717 | B1 | 1/2011 | Krebs | |
| 7,867,195 | B2 | 1/2011 | Barbut et al. | |
| 7,927,346 | B2 | 4/2011 | Vancamp et al. | |
| 7,993,324 | B2 | 8/2011 | Barbut | |
| 8,157,767 | B2 * | 4/2012 | Rozenberg et al. | 604/98.01 |
| 8,167,923 | B2 | 5/2012 | Barbut et al. | |
| 2001/0004644 | A1 * | 6/2001 | Levin | 514/646 |
| 2006/0207594 | A1 * | 9/2006 | Stenzler et al. | 128/204.18 |
| 2008/0033412 | A1 | 2/2008 | Whelan et al. | |
| 2009/0196930 | A1 | 8/2009 | Surber et al. | |
| 2010/0211140 | A1 | 8/2010 | Barbut et al. | |
| 2011/0028938 | A1 | 2/2011 | Barbut et al. | |
| 2011/0226241 | A1 | 9/2011 | Stenzler et al. | |
| 2013/0273179 | A1 * | 10/2013 | Barbut et al. | 424/718 |
| 2013/0273180 | A1 * | 10/2013 | Barbut et al. | 424/718 |
| 2013/0274651 | A1 * | 10/2013 | Barbut et al. | 604/26 |

OTHER PUBLICATIONS

Zhang et al., "Nitric Oxide Donors Increase Blood Flow and Reduce Brain Damage in Focal Ischemia," Journal of Cerebral Blood Flow Metabolism; 14:217-226 (1994); USA.

Terpolilli et al., "Inhalation of Nitric Oxide Prevents Ischemic Brain Damage in Experimental Stroke by Selective Dilatation of Collateral Arterioles," Circulation Research 2012—Journal of the American Heart Association; 110:727-738 (orig. publ. online Dec. 29, 2011); USA.

Charriaut-Marlangue et al., "Inhaled Nitric Oxide Reduces Brain Damage by Collateral Recruitment in a Neonatal Stroke Model," Stroke 2012—Journal of the American Heart Association; 43:3078-3084 (orig. publ. online Sep. 4, 2012); USA.

Pluta et al., "Analysis of Nitric Oxide (NO) in Cerebral Vasospasm After Aneursymal Bleeding," Reviews on Recent Clinical Trials, 2007, 2, 59-67; National Institutes of Health, Bethesda, MD, USA; Bentham Science Puublishers Ltd.; USA.

Toda, et al., "Cerebral Blood Flow Regulation by Nitric Oxide: Recent Advances," Pharmacological Reviews, 2009, 61:62-97; The American Society for Pharmacology and Experimental Therapeutics; USA.

* cited by examiner

SYSTEM AND METHOD FOR IMPROVING OUTCOME OF CEREBRAL ISCHEMIA

FIELD OF THE INVENTION

The present invention relates to a system and method for improving outcome following cerebral ischemia. In particular, the invention involves intra-nasally delivered nitric oxide for direct absorption into the cerebral circulation.

BACKGROUND OF THE INVENTION

Stroke occurs when focal cerebral ischemia is severe, prolonged or both. Brain tissue where cerebral blood flow is under 17 mls/min/100 g dies within a minute or two (core), tissue with blood flow 18-50 mls/min/100 g is viable for up to 30 minutes, and tissue with higher blood flow is potentially viable indefinitely (penumbra). Any procedure which increases perfusion to within the penumbral range may salvage brain tissue indefinitely. Cerebral perfusion augmentation early in the ischemic event has been shown to reduce infarct size and improve outcome from stroke in animal models. There are numerous methods for attempting to increase cerebral perfusion but the hemodynamic effect on actual cerebral perfusion has been inconsistent, and several of them have increased the risk of cerebral hemorrhage.

None of the existing techniques has yet been shown to improve outcome from stroke in human randomized trials. Moreover, mechanical methods designed to augment perfusion are invasive procedures requiring trained personnel, and they cannot be administered early in the course of the ischemia. Improvements over conventional therapies are thus desirable. In particular what is needed is a therapy that is non-invasive and easily administrable by first responders early in the course of ischemia.

BRIEF SUMMARY OF THE INVENTION

The shortcomings of conventional therapies are overcome by the apparatus and method for improving outcome following cerebral ischemia in a patient in accordance with the invention.

The novel invention includes the use of nitric oxide gas delivered intranasally for direct absorption into the cerebral circulation through the nasal vasculature in patients with cerebral ischemia.

In one aspect of the invention a method for improving outcome following cerebral ischemia includes delivering nitric oxide into the nasal cavity for absorption into the cerebral vasculature through the nasal vasculature, wherein said outcome following cerebral ischemia is improved.

In another aspect of the invention a method for improving outcome following cerebral ischemia includes delivering nitric oxide into the nasal cavity for absorption into the brain through the nasal vasculature; and preventing the inhalation of nitric oxide into the lungs to prevent pulmonary vasodilatation.

In a further aspect of the invention a method for improving outcome following cerebral ischemia includes delivering nitric oxide into the nasal cavity for absorption into the brain through the nasal vasculature; and preventing the inhalation of nitric oxide into the lungs such that systemic arterial levels of nitric oxide or of its metabolites are not significantly altered.

In another aspect of the invention a method for improving outcome following cerebral ischemia includes delivering nitric oxide into the nasal cavity for absorption into the cerebral vasculature through the nasal vasculature; and maintaining nitric oxide in the nasal cavity, to augment its effect on the cerebral circulation.

In a further aspect of the invention a method of improving outcome following cerebral ischemia includes delivering nitric oxide into the nasal cavity for direct absorption into the brain through the nasal vasculature; and maintaining nitric oxide in the nasal cavity to prevent significantly increasing the systemic arterial levels of the nitric oxide or of its metabolites.

In a further aspect of the invention a system for improving outcome following cerebral ischemia is provided. The system includes a source of a gas comprising nitric oxide; an elongate tubular member for insertion into a nose including at least one orifice thereon, the tubular member operably coupled to the source of a gas, the elongate tubular member configured for delivering the nitric oxide into a nasal cavity through the at least one orifice for absorption into a cerebral vasculature through a nasal vasculature; and a means for controlling flow of the gas, a concentration of the nitric oxide in the gas, or both, wherein the outcome following cerebral ischemia is improved.

In a further aspect of the invention a system for improving outcome following cerebral ischemia includes a source of a gas comprising nitric oxide; an elongate tubular member for insertion into a nose including at least one orifice thereon the tubular member operably coupled to the source of a gas, the elongate tubular member configured for delivering the nitric oxide into a nasal cavity through the at least one orifice for absorption into a cerebral vasculature through a nasal vasculature; a first occlusive member for occluding the nasal cavity anterior to the at least one orifice; and a means for controlling flow of the gas, a concentration of the nitric oxide in the gas, or both, wherein the outcome following cerebral ischemia is improved.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

Figure 1:
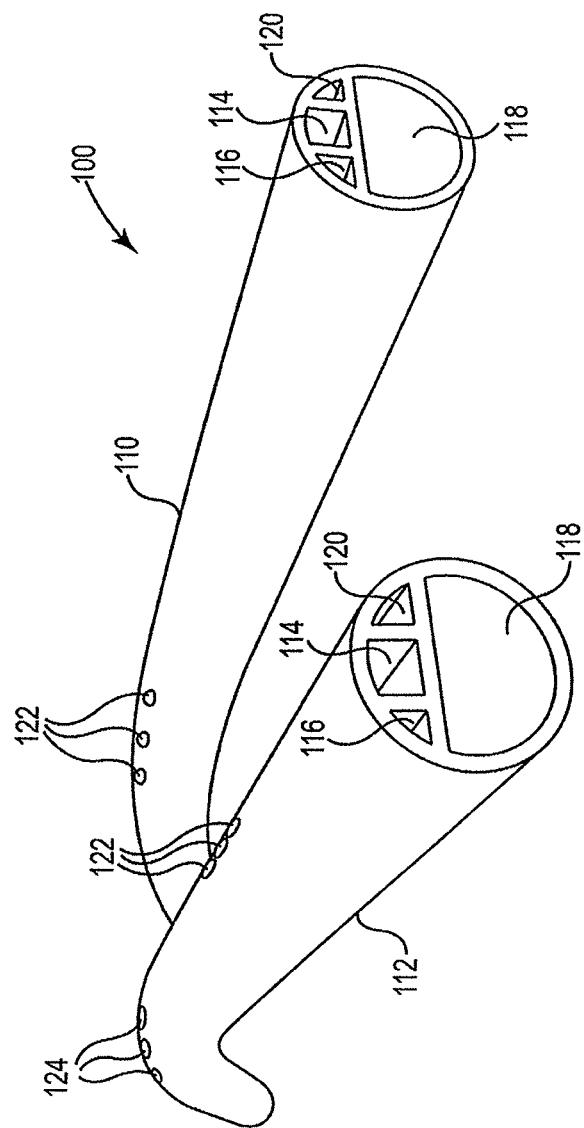
FIG. 1 is an illustration depicting an intranasal delivery catheter including a plurality of lumens in accordance with the invention.

As used herein, cerebral ischemia should be understood in its broadest sense and incorporate both focal and global cerebral ischemia. Cerebral ischemia may be caused by stroke, transient ischemia attack, traumatic brain injury, cardiac arrest, seizure, complicated migraine, memory impairment, shock, vasospasm and combinations of the foregoing.

Cerebral infarction occurs when cerebral ischemia is severe, prolonged or both. The greater the ischemia, the faster infarction occurs. Brain tissue with blood flow below a critical level (17-20 mls/mg/100 g) is referred to as the core and infarcts within minutes. Tissue with blood flow between 18-50 mls/min/100 g is viable for up to 30 minutes and tissue with a blood flow above 51 mls/min/100 g is potentially viable indefinitely. Brain tissue which is salvageable surrounding the central core is referred to as ischemic penumbra. Any procedure which increases perfusion from an initial value of <20 mls/min/100 g to a value above 50 mls/min/100 g may salvage brain tissue. Cerebral perfusion augmentation early in the ischemic event has been shown to reduce infarct size and improve outcome from stroke in animal models. Numerous methods have been described for augmenting cerebral perfusion. Pharmacologic agents such as vasopressors elevate systemic blood pressure but have inconsistent effects on cerebral perfusion. Vasodilating agents such as nitroprusside and glyceryl trinitrate can dilate cerebral vessels but do not improve cerebral perfusion, because of the concomitant reduction in systemic blood pressure. Intra-arterial nimodipine is used to treat vasospasm following subarachnoid hemorrhage but requires the presence of an interventional neuroradiologist and needs to be performed in a catheterization lab setting. Thrombectomy is a mechanical method to remove clot from an occluded vessel to improve flow in the ischemic territory, but this technique is associated with high hemorrhage rates into the core, especially in patients treated beyond the first few hours of ischemia. Furthermore, vessel occlusion is not visible angiographically in many patients. Partial aortic occlusion at the level of the renal artery has also been shown to increase cerebral perfusion during ischemia, and is not associated with increased hemorrhage rates. Sphenopalatine ganglion stimulation may also improve cerebral perfusion during ischemic events. None of the techniques mentioned have yet been shown to improve outcome from stroke in randomized trials. Furthermore, all the mechanical methods mentioned are invasive procedures requiring trained personnel. The benefit on stroke outcome from cerebral blood flow augmentation is dependent on how early in the event treatment can be initiated. Thus, novel treatments need to be non-invasive and easily administrable by first responders to be beneficial for a majority of stroke patients.

Stroke is a lay term to describe the consequence of focal ischemia. Other examples of focal cerebral ischemia include transient ischemic attacks, migraine and vasospasm following aneurismal rupture. When ischemia affects the whole brain, it is referred to as global cerebral ischemia and includes conditions such as cardiac arrest, brain trauma, and seizures. Patchy, regional cerebral blood flow reduction is also encountered in patients with memory disorders. All of these conditions would benefit from correction of the perfusion deficit in the ischemic regions.

The inventors of the present application have discovered a new non-invasive system and method for treating cerebral ischemia and improving outcome from stroke. Nitric oxide gas is delivered into the nasal cavity, for direct absorption through the nasal vasculature into the adjacent cerebral circulation. The gas may be prevented from being inhaled into the pulmonary circulation to maximize the concentration in the nasal cavity and the brain, and to prevent pulmonary vasodilation, systemic absorption, hypotension or changes in coagulation.

The method of treating stroke in accordance with the invention has not previously been described. The method in accordance with the invention is non-invasive and avoids many of the complications associated with nitric oxide inhalation while enhancing its effect on the cerebral vasculature. In a first method in accordance with the invention the vasodilator gas alone or in combination with a second gas is delivered intra-nasally for prolonged periods of time without reduction in pulmonary resistance and without systemic absorption. The second gas may be selected from the group consisting of hydrogen, xenon, oxygen, nitrogen, nitrous oxide, other vasodilator gases, air and combinations of the foregoing. The treatment selectively increases cerebral perfusion and may also be neuroprotective in the treatment of cerebral ischemia or cerebral trauma.

Nitric oxide is a neurotransmitter and a potent vasodilator substance naturally made by vascular endothelium everywhere, and by perivascular neurons in the brain. It plays a vital role in maintaining and adjusting basal vascular tone systemically and in the cerebral circulation. Changes in cerebral blood flow brought about by $CO_2$ or oxygen administration, and alternatively, by somatosensory stimulation, are all mediated by intrinsic nitric oxide. Conversely, intrinsic nitric oxide levels are diminished during cerebral ischemia or trauma, because of endothelial dysfunction. Replenishing nitric oxide to the cerebral vessels during injury may improve the cerebral circulation and reduce the damage caused by toxic metabolites. The foregoing may be achieved by delivering extrinsic nitric oxide gas close to the cerebral vessels.

Inhaled extrinsic nitric oxide is approved for use in persistent pulmonary hypertension of the newborn, to dilate the pulmonary vasculature. It is also widely used in adults in respiratory failure from a variety of causes. Inhaled extrinsic nitric oxide rapidly binds hemoglobin and is therefore effectively neutralized as it enters the systemic circulation from the lungs. This makes inhaled extrinsic nitric oxide a short-acting, selective vasodilator in the pulmonary circulation. When sufficiently large doses are inhaled, the small unbound fraction which becomes dissolved in the blood can cause some degree of hypotension. Furthermore, bleeding complications have been associated with inhaled nitric oxide. In the context of cerebral ischemia, neither of these is desirable. Hypotension may reduce cerebral perfusion pressure rather than increasing cerebral blood flow, and an increased bleeding tendency may cause hemorrhagic transformation of an ischemic lesion.

The inventors have found that nitric oxide may be delivered to the cerebral circulation directly to ensure sufficient amounts reach these vessels during ischemia. Ideally, inhalation of extrinsic nitric oxide into the pulmonary circulation is prevented, because the majority of it would effectively "disappear" by binding to hemoglobin, thus never reaching the vessels in the brain and furthermore causing hypotension. Furthermore, the delivery method should be non-invasive, such that it can be performed by first responders in the setting of acute stroke. This will ensure that all patients with stroke can receive treatment not only in the emergency room but even in the ambulance. Most importantly, a simple, non-invasive, safe method for increasing perfusion can be administered very early during the course of the event, increasing the likelihood of therapeutic success.

The nasal cavity is designed to filter out particulate matter in inhaled air and to increase the temperature of inhaled cold air, in addition to enabling smell. The convolutions in the nasal conchae provide a large surface area over which this can occur. Below the nasal mucosa, a rich plexus of arterio-venous capillaries provide a means for temperature regulation as well as gas exchange. This vascular plexus drains into the deep venous plexus of the brain, and connects with the intracranial arterial circulation. Gases entering the nasal circulation could thus enter the cavernous sinus and the Circle of Willis directly, without passing through the systemic circulation. nitric oxide is a soluble gas, and when placed in the nasal cavity, may be absorbed directly into the nasal plexus for delivery to the brain.

Figure 8:
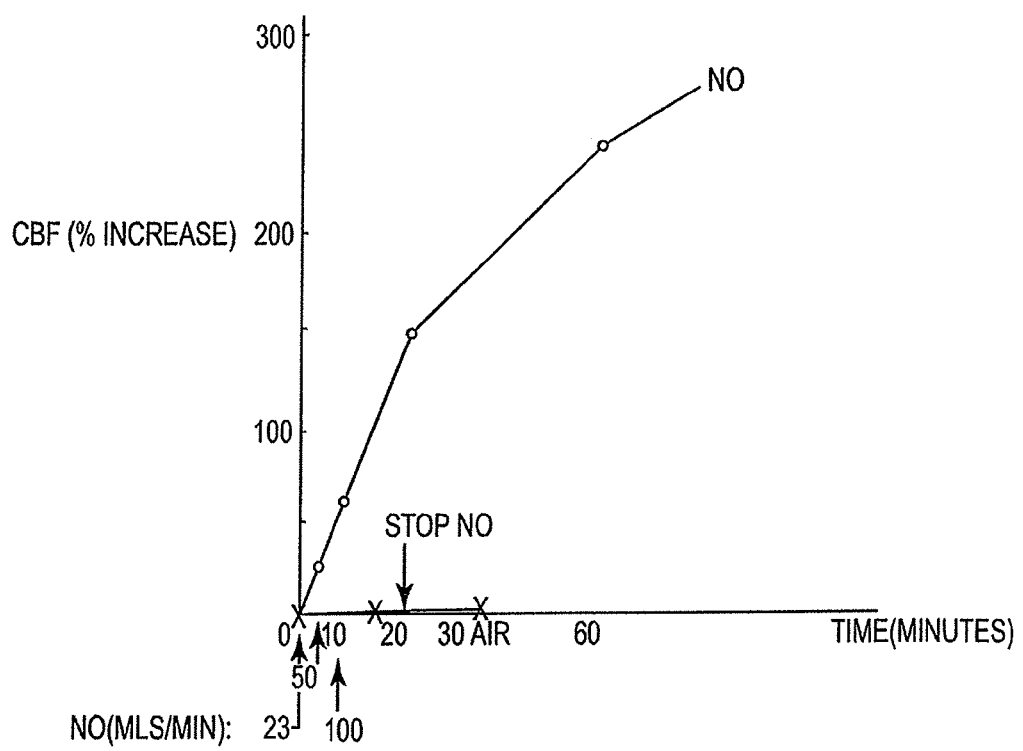
FIG. 8 is a graph demonstrating doubling of cerebral blood flow in intubated rodents using cortical laser Doppler during intranasal administration of nitric oxide.
Figure 9:
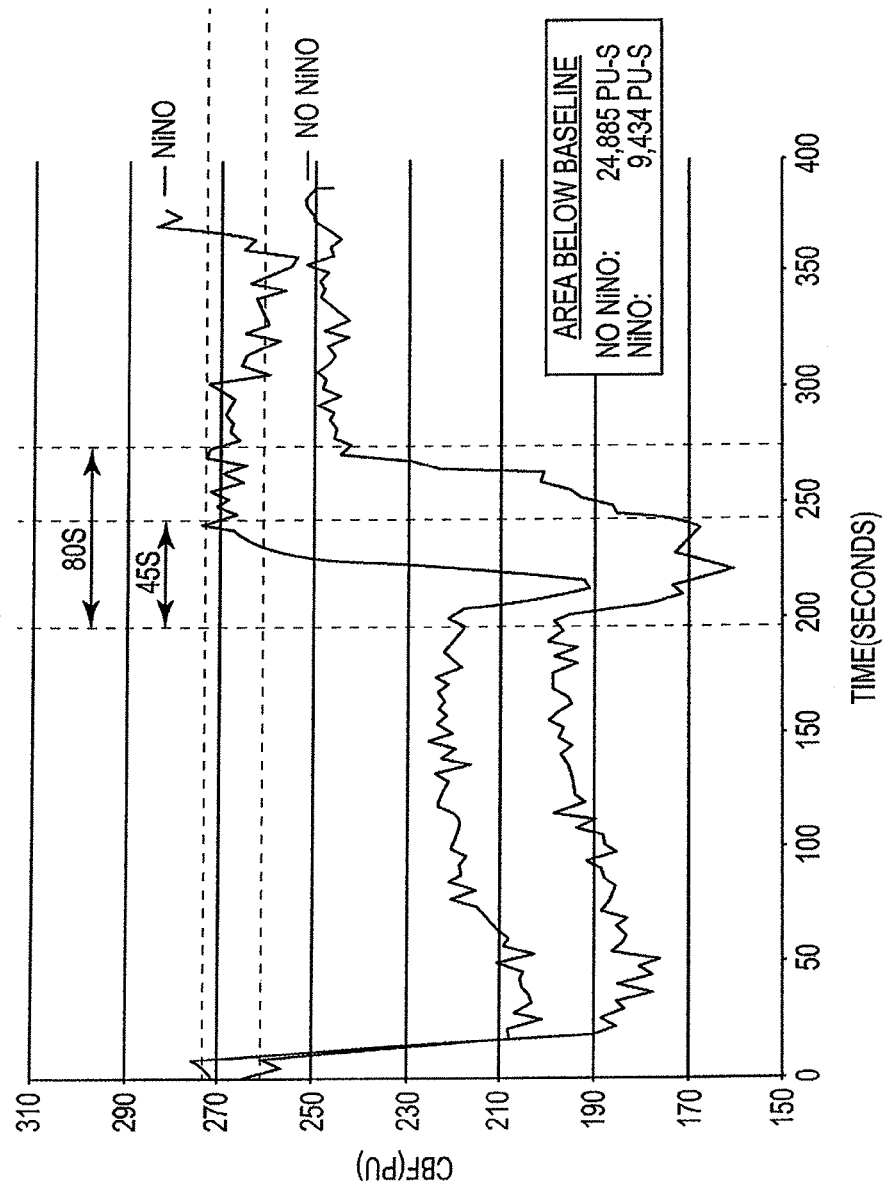
FIG. 9 is a Speckle laser Doppler tracing showing a reduction of cerebral ischemia in intubated rodents given intranasal nitric oxide.

The inventors of the present invention have demonstrated that intranasally delivered, non-inhaled nitric oxide augments cerebral blood flow in rodents. Referring to FIG. 8, a graph demonstrating the doubling of cerebral blood flow in intubated rodents using cortical laser Doppler during intranasal administration of nitric oxide is shown. In intubated rodents, the inventors have shown that cerebral blood flow increases by 100% within 60 minutes of intranasal nitric oxide delivery. The inventors have also shown, in a carotid artery occlusion model, that perfusion is improved in the ischemic hemisphere, both during the carotid occlusion and following ligature release as best seen in FIG. 9.

Figure 10:
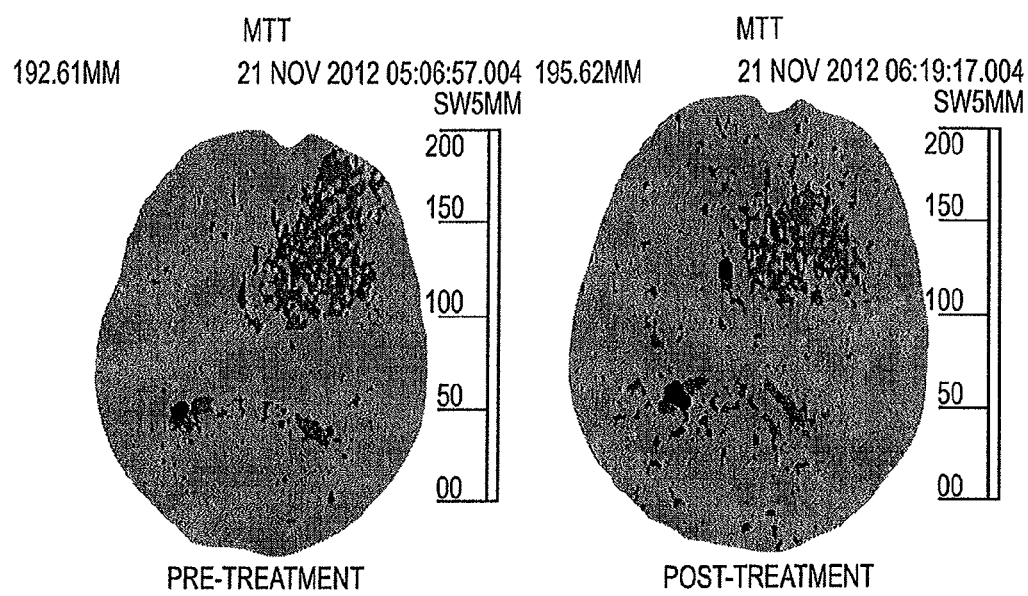
FIG. 10 is a CT perfusion scan before and after treatment with intranasal nitric oxide in a human with focal cerebral ischemia showing improvement in cerebral perfusion following treatment.
Figure 11:
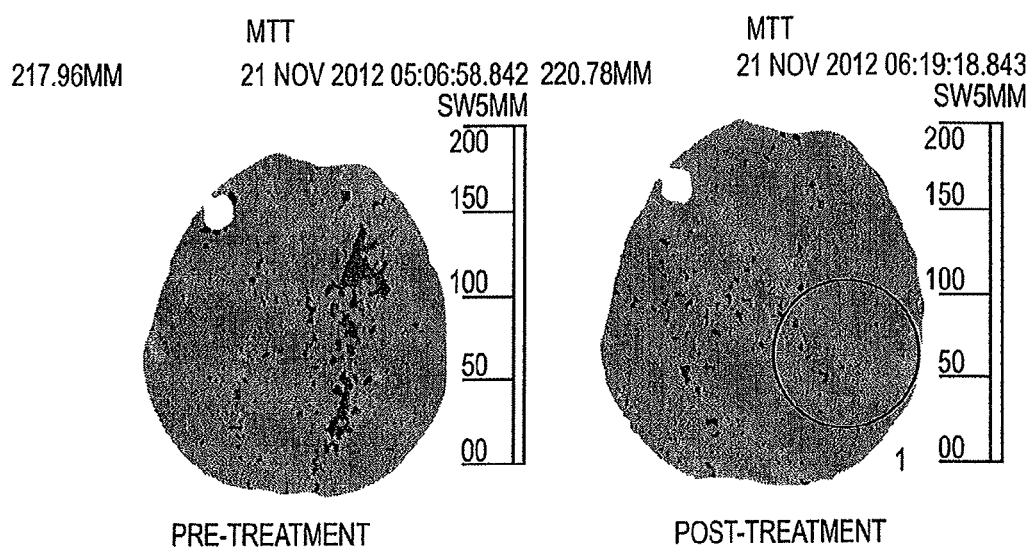
FIG. 11 is a CT perfusion scan before and after treatment with intranasal nitric oxide in a human with focal cerebral ischemia showing improvement in cerebral perfusion following treatment.

The inventors have also shown that gas treatment is tolerated at high concentration in humans when delivered intranasally and without inhalation. Furthermore, in intubated patients with cerebral ischemia, the inventors have shown augmentation of cerebral perfusion and normalization of regional perfusion abnormalities during treatment with intranasal nitric oxide using CT perfusion scanning. FIGS. 10 and 11 shown CT perfusion scans before and after treatment with intranasal nitric oxide in a human with focal cerebral ischemia showing improvement in cerebral perfusion following treatment demonstrating the foregoing.

TABLE 1

Improvement in perfusion with intranasal nitric oxide

|  |  | Right Hemisphere (normal) | Left Hemisphere (ischemic) | Changes in ACA Watershed |
|---|---|---|---|---|
| Cerebral Blood Flow | Pre Rx | 49 | 31 | 37% lower on ischemic side |
|  | Post Rx | 45 | 52 | Normalization, 67% increase in perfusion on L |
| Mean Transit Time (sec) | Pre Rx | 6 | 10 | 4 sec delay |
|  | Post Rx | 6.1 | 6.0 | Normalization |

Table I demonstrates an increase in cerebral blood flow in the ischemic hemisphere following one hour of intranasal non-inhaled nitric oxide, together with a reduction (normalization) of mean transit time (MTT) of contrast material through the ischemic hemisphere.

Given the magnitude of the cerebral blood flow response to nasally delivered nitric oxide and the small volume of the nasal cavity, the flow rates required to achieve moderate degrees of cerebral blood flow increase are actually very low-much lower than the concentration or volume required to achieve pulmonary vasodilation. In respiratory disease, the concentration of approved nitric oxide is up to 80 PPM at a minute volume of 6 L/minute. For the purposes of cerebral ischemia, the concentrations might be as low as 8 PPM or lower, more preferably 20 PPM or lower, more preferably 40 PPM or lower, more preferably 60 PPM or lower, and the volume of gas is of the order of milliliters rather than liters per minute. Increasing cerebral blood flow too much or too fast using nitric oxide might be deleterious in the treatment of stroke. Therefore both of these variables need to be tightly monitored to achieve the desired effect. Similarly, sudden discontinuation of the gas (especially if given at low concentration or volume) might decrease cerebral blood flow too fast and cause worsening of symptoms. Lastly, the amount of inhaled nitric oxide needed to increase cerebral blood flow is orders of magnitude higher than intranasal nitric oxide because it binds hemoglobin in the lungs and only tiny amounts ever reach the brain. Alternatively, limitations to the amount of nitric oxide that can be given systemically for fear of hypotension might well result in no or very limited increases in cerebral blood flow.

Increase in cerebral blood flow is attributable to focal intranasal or intra-oral effect of nitric oxide rather than to systemic absorption of the gas. When air, rather than nitric oxide is delivered intra-nasally and without inhalation, cerebral blood flow does not increase as best seen in FIG. 9. The effect on cerebral blood flow during intranasal delivery of nitric oxide with concomitant air inhalation into the lungs is therefore a focal effect on intranasal and intracranial vasculature attributable specifically to nitric oxide. Nitric oxide delivered into the nasal cavity did not enter the pulmonary circulation because both the animals and human patients were intubated and access from the nasopharynx or oropharynx to the trachea was mechanically blocked. In a non-intubated patient, nitric oxide inhalation can be prevented by occluding the nasal cavity anterior or posterior to the site of gas delivery. This is achieved by means of an anterior occlusion device such a rigid member, an expandable member, a compressible member, a sponge, a porous member, a plug, a balloon, foam and/or combinations of the foregoing, which prevent inhalation through the nostrils while maintaining a high concentration of nitric oxide in the nasal cavity. A non-intubated patient may be allowed to inhale air into the lungs during nitric oxide delivery into the nasal cavity by an optional central lumen with the distal orifice beyond the sites of nasal gas delivery and occlusion device. This focal trans-nasal penetration of nitric oxide to exert cerebral vasodilation and cerebral blood flow increase has not been previously demonstrated and is fundamental to the discovery set forth in this patent.

While nitric oxide may be given intranasally and without inhalation into the lungs to intubated, comatose individuals the tolerability of intranasal nitric oxide in awake humans has not previously been investigated. The inventors have tested the effect of nitric oxide in humans (normal volunteers) during intranasal delivery. Nitric oxide in concentrations up to 100 PPM does not elicit any sensation during intranasal delivery. Therefore it can easily be tolerated by awake, non-intubated patients.

The present invention delivers nitric oxide or a combination of nitric oxide with other gases into the nasal cavity but prevents its inhalation for the purposes of increasing cerebral blood flow and improving outcome from cerebral ischemia. Those of skill in the art will appreciate that other gases containing a combination of nitrogen and oxygen may also be used. Inhalation can be prevented by occluding the nostrils while delivering the nitric oxide to the nasal cavity. Since the volume of the nasal cavity is only approximately 150 mL, low flows are able to completely fill the nasal cavity and still replenish any that may leak out via the choana into the nasopharynx keeping the nitric oxide concentration in the nasal cavity very near the concentration of the instilled gas. For example, if 50 mL/min of 100 ppm nitric oxide is instilled into the nasal cavity and the minute volume of the patient is 7.5 L/min, the effective concentration of nitric oxide getting to the lungs assuming all occlusion mechanisms failed would still only be: 100×(50/7500)=0.67 ppm, which is <1% of that in the nasal cavity.

The passage of the gases into the lungs may be prevented by placing a nasal "clip" or otherwise occluding the entrance to the nostrils, proximal to where the gas is delivered and delivering small enough quantities which, even in the case of leakage, will be so significantly diluted by respiratory gases to not have any effect on the systemic circulation. In one aspect of the invention using an anterior occlusion device, the gas may escape via a valve or exit tube or be suctioned out into a vacuumed container.

In awake, non-intubated patients, the gas can be prevented from entering the lungs by occluding the naris (or nares) posterior to the gas delivery site. This can be achieved by means of inflatable balloons or other similar occlusion devices as disclosed herein. In an alternative embodiment, an intranasal delivery catheter may consist of a wide-bore central lumen through which the patient can inhale air into the lungs, while a smaller outer lumen with pores/perforations proximal to the occluding balloon delivers nitric oxide into the nasal cavity.

Referring now FIGS. 1 through 7, the system and method in accordance with the invention will be described. FIG. 1 is an illustration depicting first and second intranasal delivery catheters 100 in accordance with the invention. First intranasal delivery catheter 110 is used in one naris and second intranasal delivery catheter 112 is used in the second naris. Each intranasal delivery catheter 110, 112 includes a plurality of lumens therewithin namely a lumen for the delivery of nitric oxide 114, an optional lumen 116 for inflation of a posterior occlusion device (not shown), a "breath through" or optional lumen for the delivery of air to a patient's lungs 118 and optional suction lumen 120 for removal of excess nitric oxide from the nasal cavity that has not been absorbed directly into the cerebral vasculature. If suction lumen 120 is included in the catheter delivery design then suction orifices 122 are fluidly coupled to suction lumen 120 which in turn may be coupled to a one-way valve. Nitric oxide orifices 124 (not shown on intranasal delivery catheter 110) are fluidly coupled to nitric oxide lumen 114 and a source of nitric oxide. As noted, those of skill in the art will appreciate that the breath through 118 for delivery of air to a patient's lungs may be eliminated as well as the suction lumen 120 depending on the particular delivery catheter needed for any particular circumstance. Those of skill in the art will appreciate that the number of nitric oxide and suction orifices can be greater or fewer than as depicted in the FIGS. and the size of the orifices may vary with the application. In addition, suction orifices may be included on a first intranasal delivery device while the nitric oxide orifices may be included on the second delivery or they may be included on the same intranasal delivery device. Many alternatives exist for the number and size of the orifices and the present FIGS. are by way of illustration and not of limitation.

Figure 2:
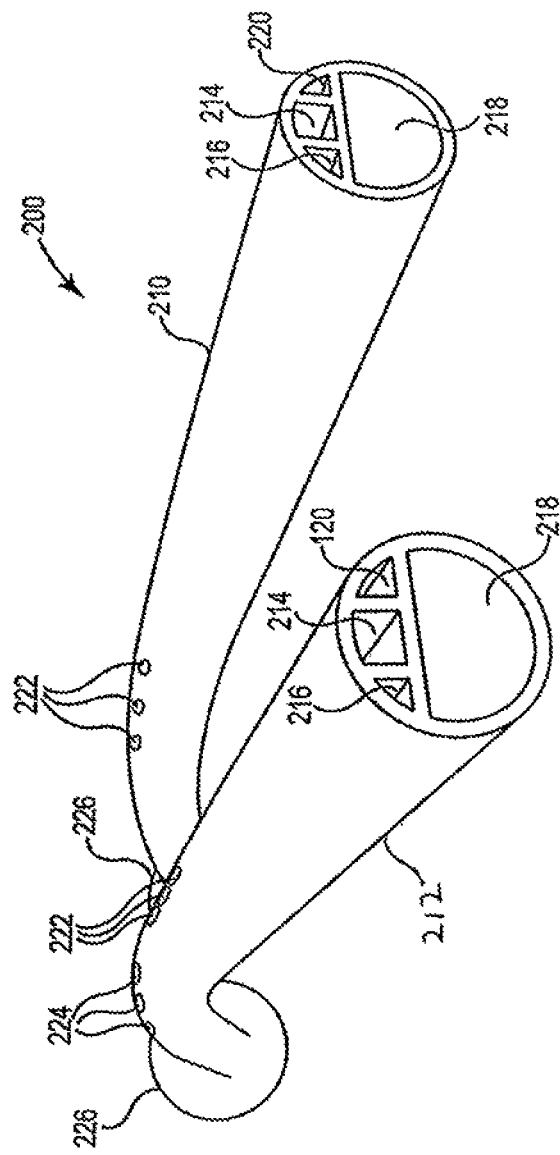
FIG. 2 is an illustration depicting an intranasal delivery catheter including a plurality of lumens and further depicting posterior nasal occlusion in accordance with the invention.

Referring now to FIG. 2 an intranasal delivery catheter depicting a posterior nasal occlusion in accordance with the invention. Like features are numbered with like numerals. First intranasal delivery catheter 210 is used in one naris and second intranasal delivery catheter 212 is used in the second naris. Each intranasal delivery catheter 210, 212 includes a plurality of lumens therewithin namely a lumen for the delivery of nitric oxide 214, an optional lumen 216 for inflation of a posterior occlusion device 226, a "breath through" or optional lumen for the delivery of air to a patient's lungs 218 and optional suction lumen 220 for removal of excess nitric oxide from the nasal cavity. If suction lumen 220 is included in the catheter delivery design then suction orifices 222 are fluidly coupled to suction lumen 220. Those of skill in the art will appreciate that suction orifices 222 and suction lumen 220 may be included on both delivery catheters 210, 212 or may be included on the first delivery catheter 210 while being eliminated from the second delivery catheter 212 and vice versa and still be within the scope of the invention. Similarly, nitric oxide orifices 232 may be include on both delivery catheters 210, 212 or on one delivery catheter while being eliminated from the other delivery catheter. The entire apparatus may also be modified such that the gas is only delivered through one nostril since such small volumes are required to increase cerebral blood flow and cerebral vasodilation. In such a case, only one nostril would need to be occluded to prevent inhalation, while the patient would be free to breathe in the other nostril.

Figure 6:
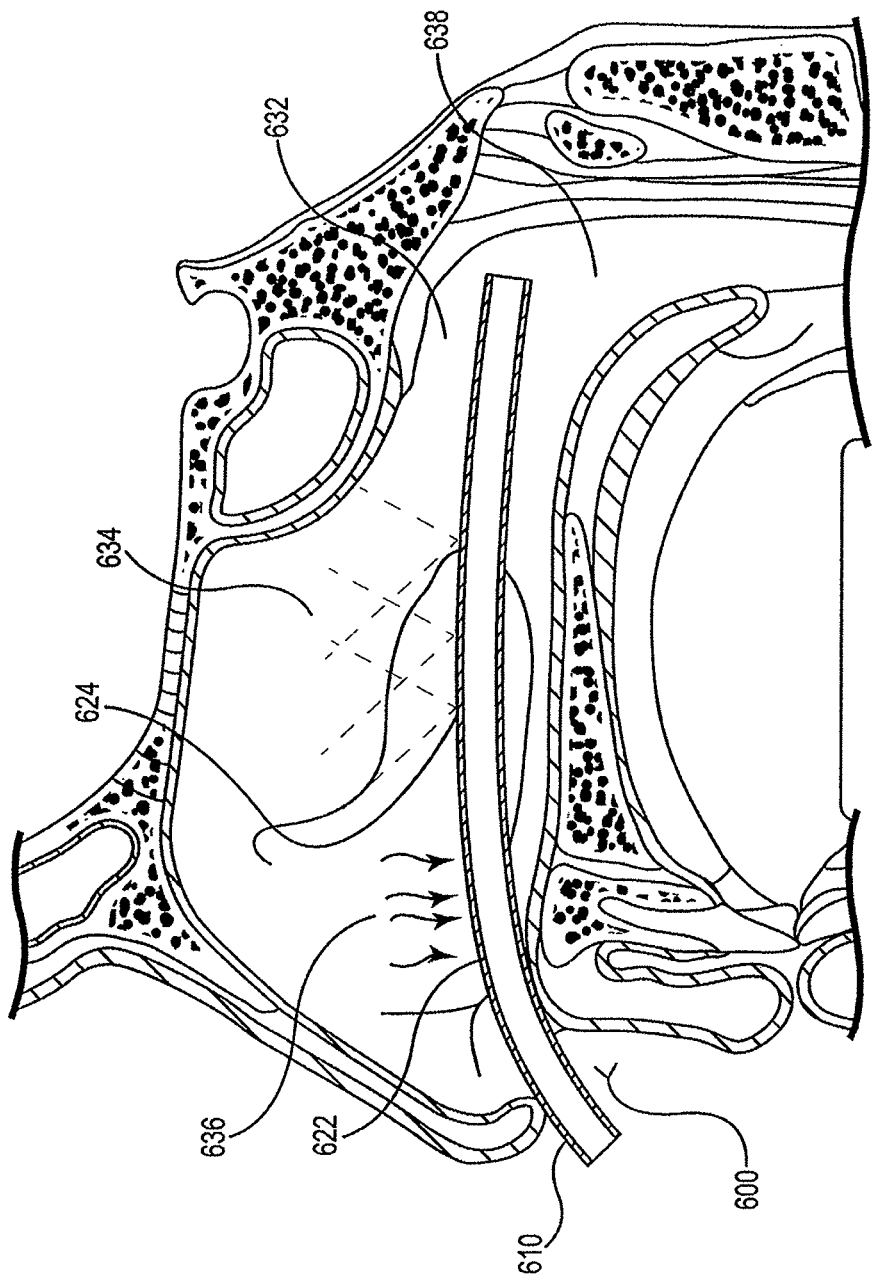
FIG. 6 is an anatomical side view of an intranasal delivery catheter including posterior nasal occlusion in a nasal cavity in accordance with the invention.

Nitric oxide orifices 224 (not shown on intranasal delivery catheter 210) are fluidly coupled to nitric oxide lumen 214 and a source of nitric oxide. As noted, those of skill in the art will appreciate that one or both of the breath through 218 for delivery of air to a patient's lungs and/or the suction lumen 220 may be eliminated depending on the particular delivery catheter needed for any particular circumstance. Posterior occlusion device 226 is positioned at the distal end of the delivery catheters 210, 212 anterior to the choana and posterior to the nitric oxide orifices 224. When positioned in the nasal cavity of a patient, posterior occlusion device 226 blocks any nitric oxide that may build up in the nasal cavity from entering the nasopharynx and lungs as best seen in FIG. 6. Posterior occlusion device 226 may comprise a rigid member, an expandable member, a compressible member, a sponge, a porous member, a plug, a balloon, foam and combinations of the foregoing. Those of skill in the art will appreciate that if a non-inflatable posterior occlusion device 226 is utilized, the inflation lumen 216 in the catheter delivery device may be eliminated.

Figure 3:
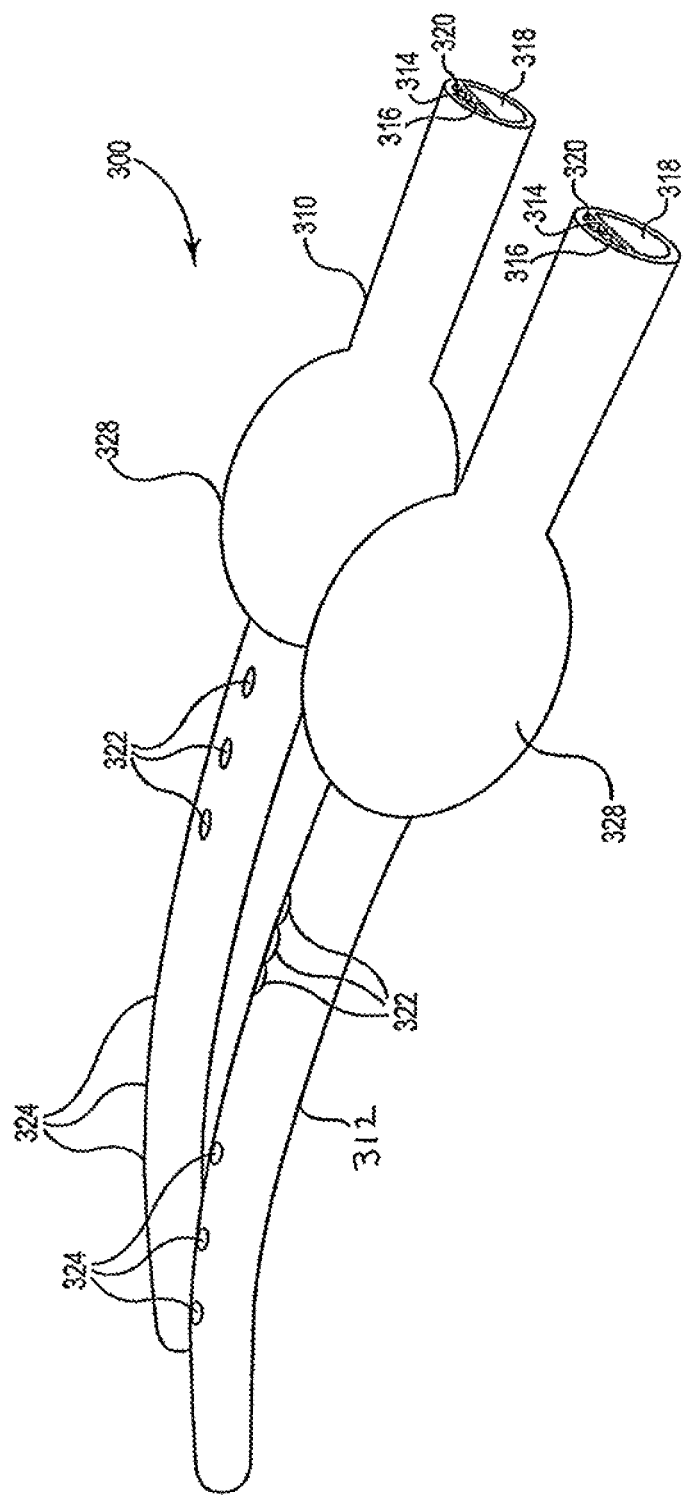
FIG. 3 is an illustration depicting an intranasal delivery catheter including a plurality of lumens and further depicting anterior nasal occlusion in accordance with the invention.

Referring now to FIG. 3 an intranasal delivery catheter 300 depicting an anterior nasal occlusion in accordance with the invention. Like features are numbered with like numerals. As noted previously, first intranasal delivery catheter 310 is used in one naris and second intranasal delivery catheter 312 is used in the second naris. Each intranasal delivery catheter 310, 312 includes a plurality of lumens therewithin namely a lumen for the delivery of nitric oxide 314, an optional lumen 316 for inflation of an anterior occlusion device 328 (in embodiments in which an inflatable anterior occlusion device is utilized), a "breath through" or optional lumen for the delivery of air to a patient's lungs 218 and optional suction lumen 220 for removal of excess nitric oxide from the nasal cavity. If suction lumen 220 is included in the catheter delivery design then suction orifices 322 are fluidly coupled to suction lumen 220. Those of skill in the art will appreciate that suction orifices 322 and suction lumen 320 may be included on both delivery catheters 310, 312 or may be included on the first delivery catheter 310 while being eliminated from the second delivery catheter 312 and vice versa and still be within the scope of the invention. Similarly, nitric oxide orifices 324 may be include on both delivery catheters 310, 312 or on one delivery catheter while being eliminated from the other delivery catheter and one of the lumen for delivering the nitric oxide similarly eliminated. Nitric oxide orifices 324 are fluidly coupled to nitric oxide lumen 314 and a source of nitric oxide. As noted, those of skill in the art will appreciate that one or both of the breath through 318 for delivery of air to a patient's lungs and/or the suction lumen 320 may be eliminated depending on the particular delivery catheter needed for any particular circumstance. Anterior occlusion device 326 is positioned at the proximal end of the delivery catheters 310, 312 to occlude the nasal cavity anterior to the nitric oxide orifices 324 and allows the nitric oxide to build up in the nasal cavity but prevents it from exiting the flares. Anterior occlusion device 328 may comprise a rigid member, an expandable member, a compressible member, a sponge, a porous member, a plug, a balloon, foam and combinations of the foregoing.

Figure 4:
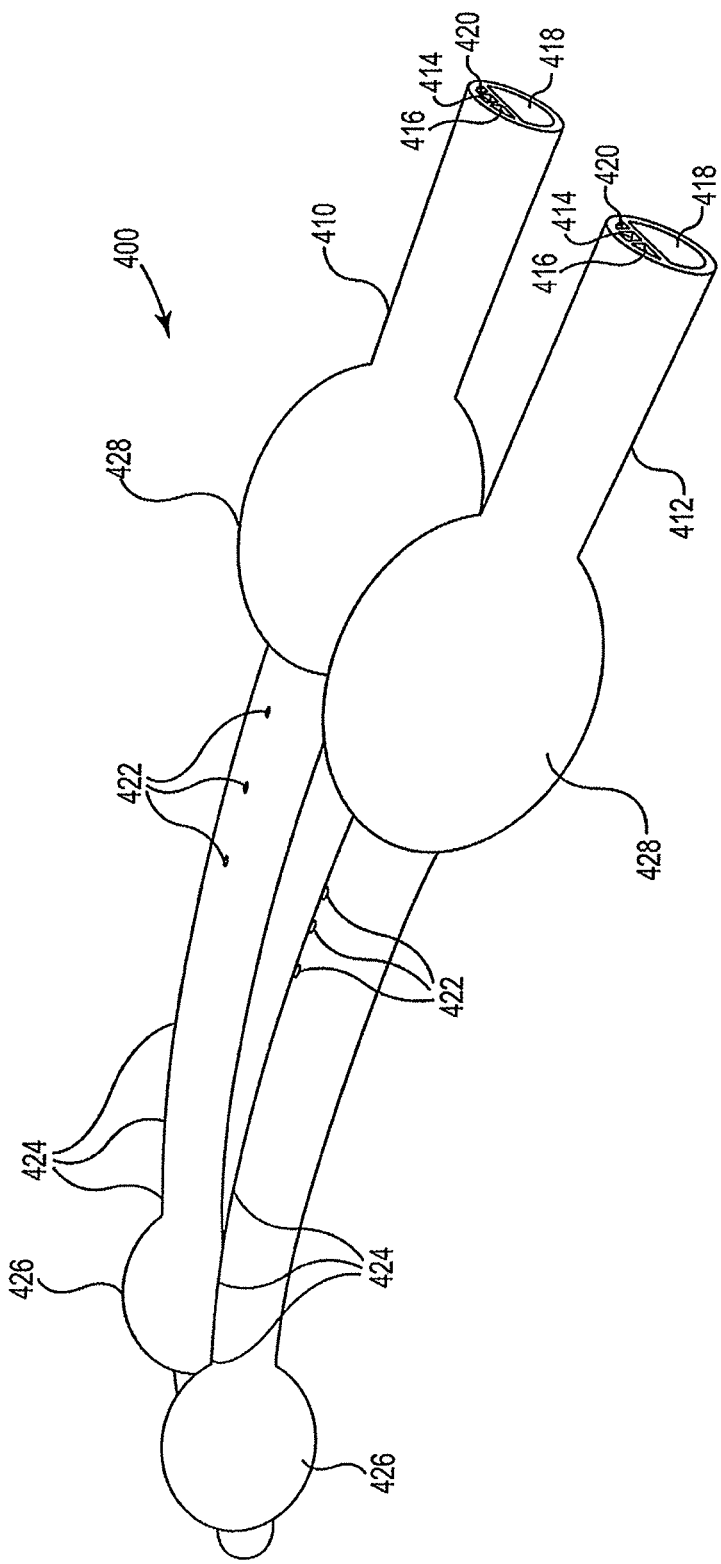
FIG. 4 is an illustration depicting an intranasal delivery catheter including a plurality of lumens and further depicting a posterior and anterior nasal occlusion in accordance with the invention.

Referring now to FIG. 4 another aspect of an intranasal delivery catheter 400 depicting anterior and posterior nasal occlusion devices 428, 426 in accordance with the invention is shown. Like features are numbered with like numerals. Those of skill in the art will appreciate that the intranasal delivery catheter 400 depicted in FIG. 4 may be modified by the elimination of certain elements and features as previously discussed and still fall within the intended scope of the invention.

Figure 5:
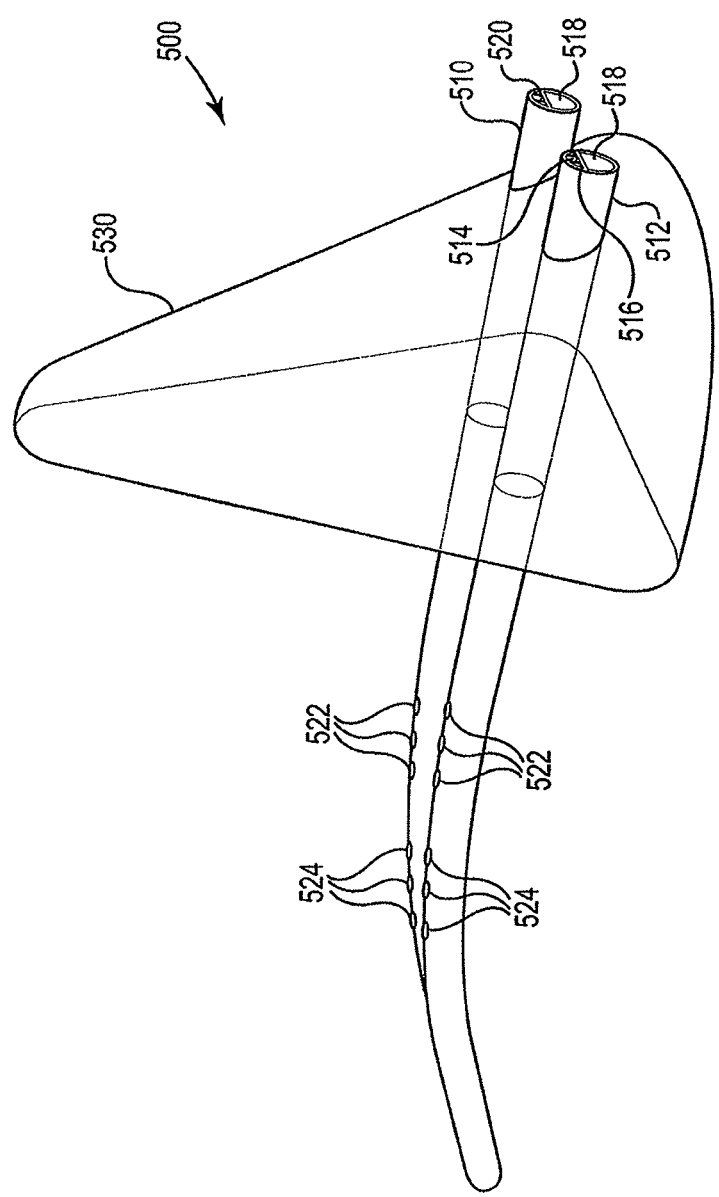
FIG. 5 is an illustration depicting an intranasal delivery catheter showing a plurality of lumens and further depicting an external anterior nasal occlusion in accordance with the invention.

FIG. 5 depicts another aspect of an intranasal delivery catheter 500 including an anterior occlusion device comprising a mask 530. Like elements are numbered with like numerals. Those of skill in the art will appreciate that the intranasal delivery catheter 500 depicted in FIG. 5 may be modified by the elimination of certain elements and features, such as the air breath through lumen 518, suction orifices 522 and suction lumen 520 and/or the first and/or second delivery catheters 510, 512 as previously discussed and still fall within the intended scope of the invention. Those of skill in the art will also appreciate that anterior occlusion device 530 will allow minimal inhalation of nitric oxide into the lungs. If it is desirable to prevent inhalation of nitric oxide into the lungs a posterior occlusion device (as best seen in FIGS. 2 and 4) may be added.

Turning now to FIG. 6 an anatomical side view including an exemplary embodiment of an intranasal delivery catheter 610 including a posterior nasal occlusion device 632 positioned in a nasal cavity 634 in accordance with the invention is depicted. As can be seen intranasal delivery catheter 610 includes suction orifices 636 and nitric oxide orifices 624. The buildup of nitric oxide in the nasal cavity for absorption into the cerebral vasculature through the nasal vasculature can be seen. Excess nitric oxide is removed from the nasal cavity through suction orifices 622 operably coupled to suction means on an external control device (not shown). Posterior occlusion device 632 may comprise a rigid member, an expandable member, a compressible member, a sponge, a porous member, a plug, a balloon, foam or combinations of the foregoing. Posterior occlusion device 632 is positioned anterior to the choana and posterior to the nitric oxide orifices 622 and the delivery of nitric oxide thus allowing the concentration of nitric oxide to build up in the nasal cavity without inhalation into the lungs.

Figure 7:
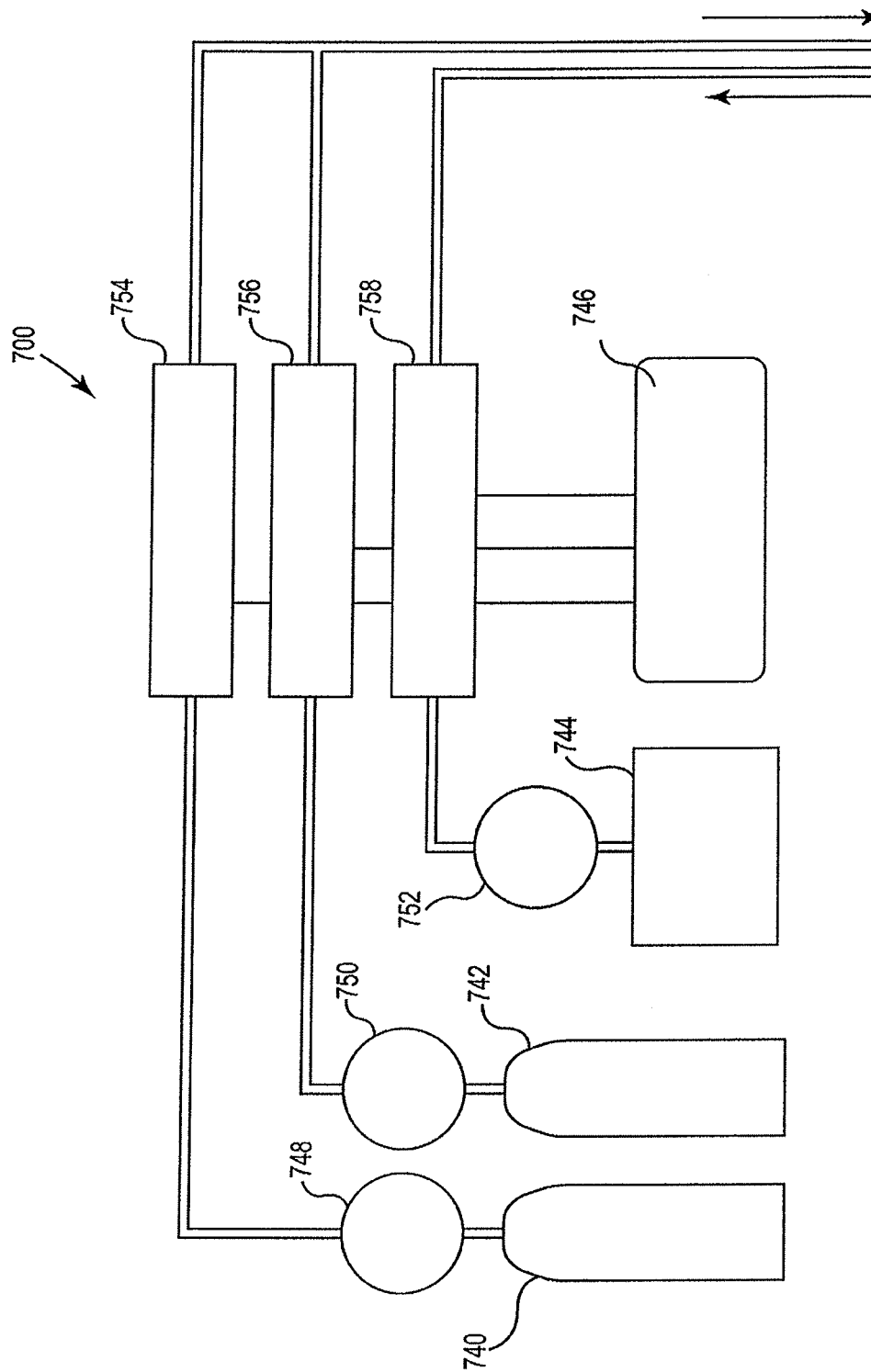
FIG. 7 is a schematic diagram of a means for controlling gas flow and concentration in accordance with the invention.

Referring now to FIG. 7 a schematic diagram of a means for controlling gas flow and concentration in accordance with the invention is depicted. The means for controlling gas flow includes a source of nitric oxide 740 fluidly coupled to the nitric oxide lumen of the intranasal delivery catheter, an optional source of a second gas 742, an optional vacuum means fluidly coupled to the suction lumen in the intranasal delivery catheter in accordance with the invention. Those of skill in the art will appreciate that if a second gas is used then the source may be fluidly coupled to the nitric oxide lumen of the intranasal delivery catheter for delivery with the nitric oxide. Alternatively the source of second gas 742 may be fluidly coupled to an additional "second gas" lumen in the intranasal delivery catheter (not shown) where the mixing of the two gases may occur inside the nasal to prevent oxidation of nitric oxide during low flow delivery rather than in the intranasal delivery catheter as above. The gases may be allowed to mix prior to delivery or at the point of delivery. Volatile anesthetics, arginine, an nitric oxide precursor, and other gases such as hydrogen or nitrous oxide may also increase cerebral blood flow when delivered into the nasal cavity.

A one way valve (not shown) may be included in the suction line to prevent inhalation while allowing excess nitric oxide with or without a second gas to be extracted from the nasal cavity with optional suction means, as shown. The source of nitric oxide 740 and source of second gas 742 are each operably coupled to pressure regulators 748, 750 and the vacuum means is coupled 744 is operably coupled to vacuum regulator 752.

Mass flow controllers 754, 756, 758 are operably coupled to the pressure regulators 748, 750 and vacuum regulator 752 and the source of nitric oxide 740, source of second gas 742 and vacuum means 744, respectively, to measure and control the flow of the gases and vacuum. Electronic control means 746 is operably coupled to mass flow controllers to monitor and control the flow of gas and the concentration of gas being delivered to the intranasal delivery catheter in accordance with the invention.

Those of skill in the art will appreciate that the system and method in accordance with the invention may be modified to incorporate a humidifier and warmer into the circuit to adjust the humidity and temperature of the gas mixture.

Those of skill in the art will also appreciate that the cerebral blood flow increase needs to be adjusted carefully. Firstly, the degree of cerebral blood flow increase required will vary from patient to patient, depending on the state and number of existing patent collaterals, size of stroke, size of penumbral tissue, degree of ischemia within the penumbra, time from symptom onset and symptomatic relief. Should the presenting symptom be hemiplegia, and should the hemiplegia recover with a 30% increase in cerebral blood flow, then the flow rates and the gas concentration required to get there needs to be maintained and not increased. Similarly, should stable symptoms at a given gas dose and cerebral blood flow increase suddenly start deteriorating; gas dose (flow rate or concentration or both) should be increased. Or if symptoms are stable for a while, gas dose should be reduced until such level as symptoms recurred. This might mean switching off the gas delivery altogether intermittently. The cerebral blood flow may be measured using cerebral oximetry, other non-invasive laser-Doppler techniques or transcranial Doppler, SPECT, CT or MR perfusion or other imaging techniques. This information may be fed back into the device and the dose adjusted accordingly. Cortical activity may also be measured over the ischemic territory by MAG, EEG, or other electrical measuring method and this information may be fed back to adjust the dose of the gas. The discovery in this instance is the coupling of cerebral blood flow increase and of symptomatic relief to gas dosing regimen.

Furthermore, cerebral blood flow increase using intranasal nitric oxide may be coupled with techniques which increase cortical demand for blood, to further channel the increased delivery towards the ischemic regions. Such techniques to increase cortical demand may be peripheral stimulation in the affected domain, sensory, motor, visual, auditory, and the like or it may be direct cortical electrical or other stimulation over the affected cortex. In turn, this may be achieved using transcortical magnetic stimulation or ultrasound or epidural or subdural direct cortical stimulation. The discovery in this instance is the coupling of nitric oxide delivery to the cerebral blood flow or cortical electrical response observed.

Cortical electrical activity is typically coupled to regional blood flow. So cortical electrical activity may be measured directly and fed back into the device to alter drug delivery. Once cortical electrical activity normalized, the dose maybe progressively reduced and even discontinued. Contrarily, if a fairly normal cortical recording were to diminish or disappear or become abnormal in some other way, the dose of drug delivery maybe increased automatically.

Cerebral blood flow increase may be further modified by modifying the temperature and humidity of the delivered gas. By way of example, increasing the temperature in the nasal cavity may cause vasodilation of the nasal vasculature and increase absorption of drug focally. This may further increase cerebral blood flow or serve to reduce the dose required to achieve any given cerebral blood flow increase. Similarly, increasing the humidification in the nasal cavity may serve to increase drug delivery and reduce the dose required to attain any given cerebral blood flow increase. Therefore, both of these parameters may be fed back to the device to adjust gas delivery accordingly.

Cerebral oximetry, brain temperature, regional oxygen or glucose consumption can also be used as alternate measures of treatment efficacy and delivery parameters modified accordingly. Regional metabolic consumption, such as oxygen or glucose consumption and brain temperature typically increase as cortical activity, cerebral blood flow or cortical stimulation increase. All these factors can be fed back into the device and gas delivery adjusted accordingly.

Various modifications and additions may be made to the exemplary embodiments disclosed herein without departing from the scope of the invention. For example, while the embodiments disclosed herein refer to particular features, the scope of this invention also includes embodiments having different combinations of features and embodiments that do not include all of the described features. Accordingly, the scope of the present invention is intended to embrace all such alternative, modifications and variations as fall within the scope of the claims and equivalents thereof.

What is claimed is:

1. A system for improving outcome following cerebral ischemia comprising:
    a source of a gas comprising NO;
    an elongate tubular member defining at least first, second, third and fourth fluidly separated lumens, at least one orifice positioned on an outer surface of said elongate tubular member and in fluid communication with said at least first lumen and said source of NO gas, and an occlusive member operably coupled to said elongate tubular member, said at least first lumen configured for delivering said NO into a nasal cavity through said at least one orifice for absorption into a cerebral vasculature through a nasal vasculature, said at least second lumen configured to deliver a source of oxygen to lungs of a patient, said at least third lumen configured to inflate said occlusive member and said at least fourth lumen configured to remove excess NO from the nasal cavity, said occlusive member configured to isolate NO in the nasal cavity and prevent the inhalation of NO into the lungs; and
    a means for controlling flow of the gas, a concentration of the NO in said gas, or both, wherein said outcome following cerebral ischemia is improved.

2. The system of claim 1 wherein said elongate tubular member configured for delivering NO into the nasal cavity is configured to deliver said NO solely into the nasal cavity.

3. The system of claim 1 wherein said cerebral ischemia is caused by stroke, TIA, traumatic brain injury, cardiac arrest, seizure, complicated migraine, shock, vasospasm and combinations of the foregoing.

4. The system of claim 1 further comprising a fifth lumen having a distal opening distal to the occlusive member and a proximal opening to the atmosphere for allowing inhalation through the nose.

5. The system of claim 1 wherein said occlusive member comprises a rigid member, an expandable member, a compressible member, a sponge, a porous member, a plug, a balloon, foam or combinations of the foregoing.

6. The system of claim 1 wherein a means for controlling the flow of the gas, the concentration of the NO in said gas, or both comprises one or more flow meters; a series of valves controlled by an electronic control system whereby said valves are controlled by a feedback from said flow meters.

7. The system of claim 1, wherein a flow rate of gas is between 1-10000 mL/min.

8. The system of claim 7 wherein a flow rate of gas is between 25-1000 mL/min.

9. The system of claim 8 wherein said flow rate of gas in between 50-500 mL/min.

10. The system of claim 1 wherein said elongate tubular member comprises two elongate tubular members configured to deliver NO into both sides of the nasal cavity.

11. The system of claim 10 wherein said occlusive member comprises two occlusive members for occluding both sides of the nasal cavity.

12. The system of claim 1 wherein said elongate tubular member is configured to deliver NO into one side of the nasal cavity.

13. The system of claim 12 wherein said occlusive member comprises one occlusive member configured to occlude a same side of the nasal cavity.

14. The system of claim 1, wherein a concentration of nitric oxide is between 1 and 1000 ppm.

15. The system of claim 14, wherein the concentration of nitric oxide is between 5 and 80 ppm.

16. The system of claim 1, wherein said means for controlling the flow of the gas further comprises a means for continuously or intermittently delivering said NO.

17. The system of claim 1, wherein said means for controlling said gas includes a means a for diluting NO with one or more gases to form a mixture of gases.

18. The system of claim 17, wherein the gases are selected from air, nitrogen, oxygen, argon, helium, anesthetic gases, xenon, nitrous oxide, other respiratory gases and combinations of the foregoing.

19. The system of claim 17, wherein said means for controlling includes means for controlling a concentration of each gas individually.

20. The system of claim 17, wherein the mixture of gases is at or above room temperature during said delivering.

21. The system of claim 17, wherein the mixture of gases is humidified prior to or during said delivering.

22. The system of claim 1 further comprising a means for monitoring a physiologic parameter.

23. The system of claim 22, wherein the delivery of NO is controlled by feedback from monitoring the physiologic parameter.

24. The system of claim 23, wherein said physiologic parameter is selected from cerebral blood flow, cerebral oxygen, cortical electrical activity, spinal fluid marker and combinations of the foregoing.

25. The system of claim 1 further comprising a means for monitoring an intranasal concentration of NO.

26. The system of claim 25, wherein the delivery of said NO is controlled by feedback from the monitoring of the concentration of intranasal NO.

* * * * *